United States Patent [19]

Ferzli

[11] Patent Number: 5,171,257
[45] Date of Patent: Dec. 15, 1992

[54] LAPAROSCOPIC INSTRUMENT

[76] Inventor: George S. Ferzli, 48 Merrick Ave., Staten Island, N.Y. 10301

[21] Appl. No.: 692,422

[22] Filed: Apr. 29, 1991

[51] Int. Cl.⁵ .................................. A61B 17/00
[52] U.S. Cl. ............................ 606/205; 606/144
[58] Field of Search .......... 606/13, 19, 138–150, 606/205–209

[56] References Cited

U.S. PATENT DOCUMENTS 2,113,246 4/1938 Wappler .......................... 606/205
4,122,856 10/1978 Mosior et al. ................... 606/170

Primary Examiner—C. Fred Rosenbaum
Assistant Examiner—Manuel Mendez
Attorney, Agent, or Firm—Jordan and Hamburg

[57] ABSTRACT

A laparoscopic instrument includes an elongated member having two pairs of jaws with each pair being movable between open and closed positions. Finger grips are operably connected to each pair of jaws for actuating each pair of jaws between their open and closed positions.

19 Claims, 2 Drawing Sheets

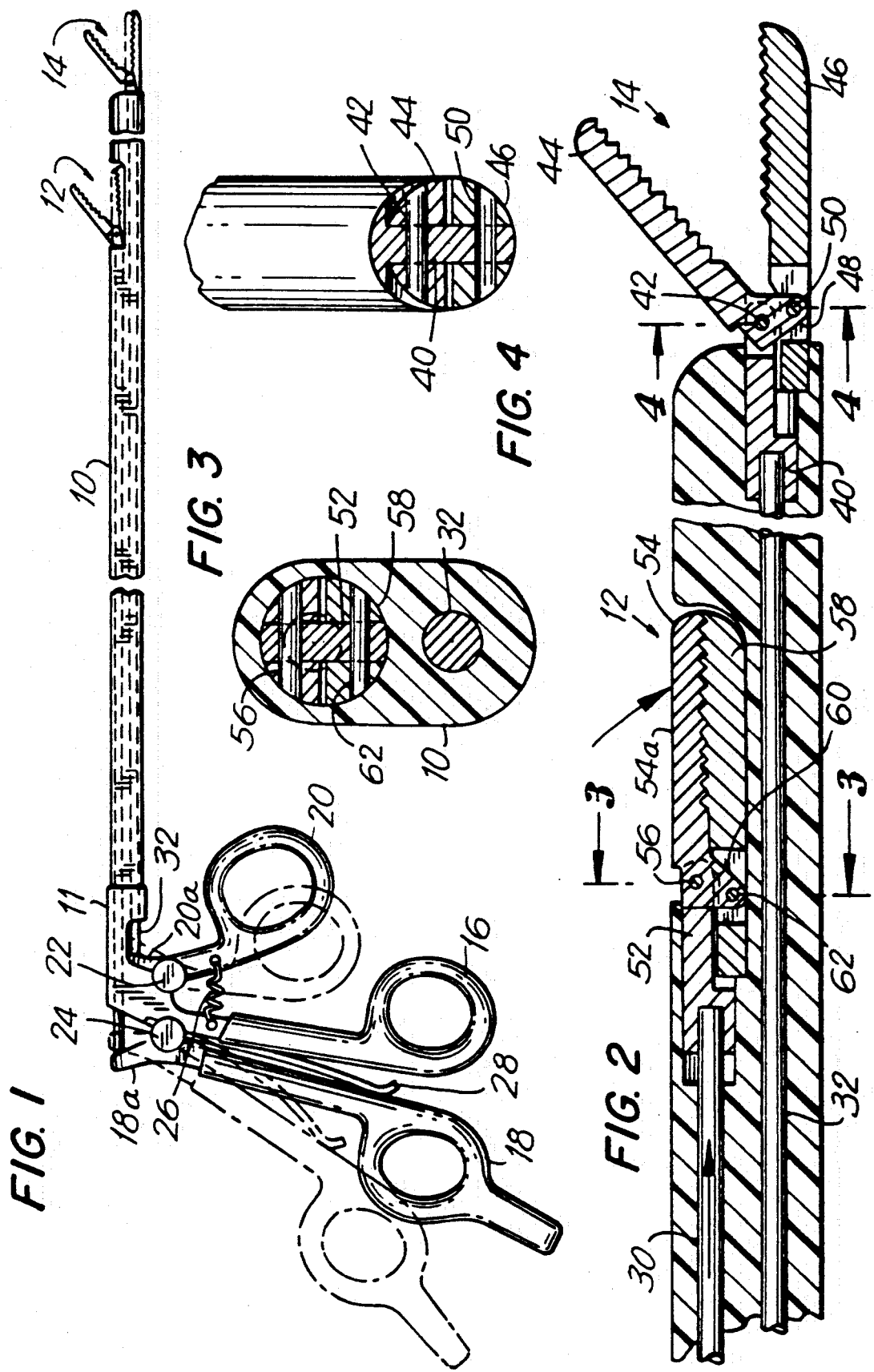

LAPAROSCOPIC INSTRUMENT

This invention relates to a laparoscopic instrument used during laparoscopic surgery.

In laparoscopic surgery, a miniature TV camera and surgical instruments are inserted through small punctures in the abdomen. The camera displays the patient's inner areas on a TV monitor which the surgeon watches while manipulating the instruments to perform the surgery. For example, laparoscopic cholecystectomy is used for removing the gallbladder. In order to remove the gallbladder, instead of making a six inch incision in the abdomen, a doctor using laparoscopy can cut a tiny incision in the abdomen and the patient's gallbladder can be pulled out through the incision. With laparoscopic surgery, there is minimal invasion such that there is a reduction in pain, fast recovery, and almost invisible scars.

The possibilities of laparoscopy is not limited to gallbladders but has also been used for ulcers, hernias, and appendectomies.

SUMMARY OF THE INVENTION

An object of the invention is to provide a laparoscopic instrument which can be inserted through a small opening in a person's body and which can be used during laparoscopic surgery for various purposes including handling of sutures and tying knots in the sutures during laparoscopic surgery.

Another object of the invention is to provide a laparoscopic instrument which facilitates handling of sutures and tying of knots during laparoscopic surgery.

A further object of the invention is to provide a laparoscopic instrument having a pair of independently operated jaw means such that a single instrument can perform more than one function during laparoscopic surgery.

The above objects and other objects of the invention are achieved by providing a laparoscopic instrument which comprises an elongated member having two pairs of jaw means with each pair being movable between open and closed positions and finger grip means operably connected to each pair of jaw means for actuating each pair between their open and closed positions.

BRIEF DESCRIPTION OF THE DRAWINGS

FIG. 1 is an elevation view of a laparoscopic instrument according to one embodiment of the invention.

FIG. 2 is a partial longitudinal sectional view on a larger scale of the right-hand portion of the laparoscopic instrument shown in FIG. 1.

FIG. 3 is a cross-sectional view taken along the line 3—3 in FIG. 2.

FIG. 4 is a cross-sectional view taken along the line 4—4 in FIG. 2.

DESCRIPTION OF THE PREFERRED EMBODIMENTS

Figure 5:
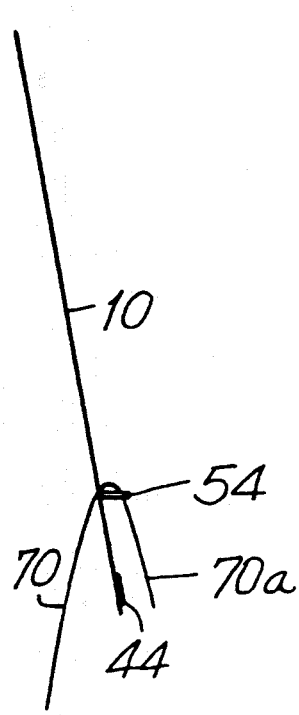
FIGS. 5 to 8 are schematic representations of one example of tying a knot in a suture using the laparoscopic instrument of the invention.

Referring to FIG. 1, the laparoscopic instrument shown therein includes an elongated barrel 10 having a pair of alligator jaws 12 and 14 at the distal end thereof and finger grips at the proximal end thereof which are grasped and operated by the surgeon's fingers for opening and closing the alligator jaws 12 and 14. The alligator jaws 12 and 14 are operable to be closed, as shown in the middle of FIG. 2, or to be opened, as shown in FIG. 1, and the right-hand portion of FIG. 2. Accordingly, the surgeon can separately open and close the two alligator jaws 12, 14 in order to grasp and hold component parts used during an operation, for example, to grasp sutures and for tying knots in the sutures.

The instrument includes three finger grips 16, 18 and 20. The finger grip 16 is stationary in that it is fixed to a barrel end support 11 fixed to the proximal end of the barrel 10. The finger grip 20, on the other hand, is pivotably mounted on the barrel end support 11 at a pivot 22 while the finger grip 18 is pivotably mounted on the barrel end support 11 at a pivot 24. A spring 26 between the pivotal finger grip 20 and the fixed finger grip 16 pivotably biases the movable finger grip 20 in a clockwise position as shown in FIG. 1 to bias the alligator jaws 14 to a closed position. A spring 28 mounted on the pivot 24 extends downwardly to engage the movable finger grip 18 to bias the movable finger grip 18 in a clockwise direction as shown in FIG. 1 to thereby bias the alligator jaws 12 in a closed position. In FIG. 1, the two alligator jaws 12 and 14 are shown in an open position and correspond to the solid line position of the finger grips 18 and 20 in FIG. 1. The broken line representation of the finger grips 18 and 20 in FIG. 1 represent the closed position of the alligator jaws 12, 14.

The barrel 10 includes the two internal passageways which slidably support actuating rods 30 and 32. The end of the actuating rod 32 is connected to an extension 20a of the finger grip 20 such that pivoting of the finger grip 20 about its pivot 22 slides the operating rod 32 in the barrel 20.

The other end of the operating rod 32 is connected to a link 40 which is slidably mounted in the barrel 10 and which has an end pivotably connected to the upper jaw 44 at the pivot 42. The lower jaw 46 is connected to the barrel 10 and an extension 48 on the upper jaw 44 is pivotably connected to an inner portion of the lower jaw 46 at the pivot 50.

With the above arrangement, it will be seen from FIG. 2 that as the rod 32 is moved to the right from the position shown in FIG. 2, the upper jaw 44 will pivot clockwise about the pivot 50 to a closed position. Movement of the rod 32 to the left, as shown in FIG. 2, will pivot the upper jaw 44 from a closed position to its open position.

With the above arrangement, it will be seen that when the finger grip 20 is pivoted counterclockwise from the broken line to the solid line position shown in FIG. 1, the jaw 44 will move from its closed to its open position.

The end of the other actuating rod 32 is connected to an extension 18a of the finger grip 18 such that rotation of the finger grip 18 about its pivot 24 slides the operating rod 30 in the barrel 10.

The other end of the actuating rod 30 is connected to a link 52 which is slidably mounted within the barrel 10 and which has an end pivotably connected to the upper jaw 54 at the pivot 56. The lower jaw 58 is connected to the barrel 10 and an extension 60 on the upper jaw 54 is pivotably connected to an inner portion of the lower jaw 58 at the pivot 62.

With the above arrangement, it will be seen from FIG. 2 that as the rod 30 is moved to the left from the position shown in FIG. 2, the upper jaw 54 will pivot counterclockwise about the pivot 62 to an open position. Movement of the rod 30 to the right, as shown in FIG. 2, will pivot the upper jaw 54 from an open position to its closed position.

With the above arrangement, it will be seen that when the finger grip 18 is pivoted clockwise from the broken line to the solid line position shown in FIG. 1, the jaw 54 will move from the closed to its open position.

With the above described arrangement, it will be seen that the surgeon is able to selectively operate the finger grips 18, 20 to independently open and close the two alligator jaws 12 and 14. In this way, the surgeon can use either alligator jaw 12 or 14 for grasping or releasing components used during the operation, for example, for grasping and releasing sutures for tying knots during a laparoscopic operation.

In addition to the above, the backside 54a of the alligator jaw 54 can be used to retain the suture during formation of a loop which is made while tying a knot. When tying a knot on a suture, it is necessary to form a loop in a length of the suture and then pass the free end of the suture through the loop to make the knot. Considering the fact that this is performed within the confines of the inside of a person's body and that the view is limited by what can be seen on a TV screen, further bearing in mind that the movements of the instruments are effected outside of the body by the grasping portion of the instrument, tying of a knot in a suture under such conditions can be a time consuming process. With the laparoscopic instrument of the present invention, the forming of a loop and a knot in a suture is greatly facilitated because as previously indicated, the loop can be passed over the backside 54a of the inner jaw 54 to support the loop as the instrument is manipulated and the other jaw 14 is used to grasp the free end of the suture and pass it through the loop to form the knot.

Figure 6:
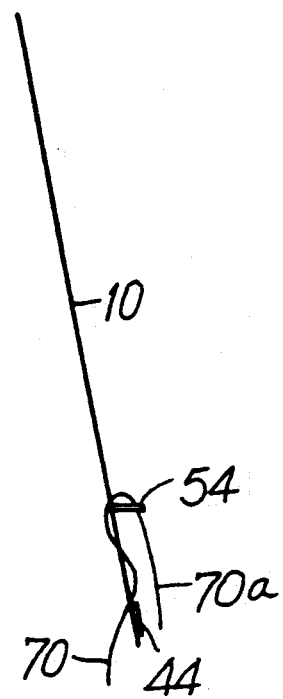
Figure 7:
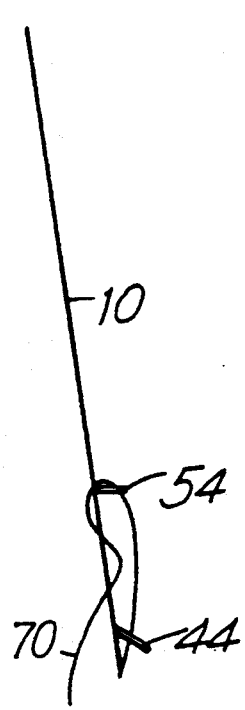
Figure 8:
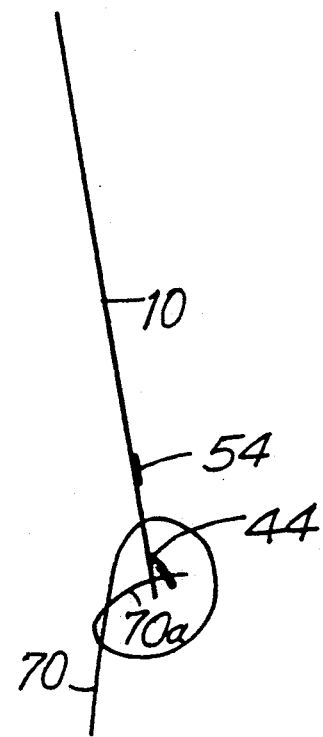

FIGS. 5 to 8 are schematic representations of one example of using the laparoscopic instrument for tying a knot in a suture. In FIG. 5 the intermediate jaw 54 is opened and the instrument manipulated to drape a suture 70 over the backside of the open intermediate jaw 54. Subsequently, the instrument is turned and manipulated to twist or wrap the suture 70 about the barrel 10 as shown in FIG. 6, and then the end jaws 44 grasps the free end 70a of the suture as shown in FIG. 7 whereupon the intermediate jaw 54 can be closed so that the grasped end 70a of the suture can be pulled through the loop 70b to make a knot as shown in FIG. 8.

Although the jaws in FIGS. 1 and 2 are shown as having serrations, the mating faces of the jaws may also have smooth surfaces. Although in the drawings the pivotal jaws 44, 54 are shown in the open position as disposed at an acute angle relative to the longitudinal axis of the barrel 10, either one or both pivotal jaws 44, 54 may be disposed perpendicular to the longitudinal axis of the barrel 10 when in their open position.

Although FIG. 3 shows an oval cross-sectional configuration of the body 10, the overall configuration may be circular.

The length of the barrel of the laparoscopic instrument is generally longer than that shown in FIG. 1 as represented by the break in the longitudinal central part of FIG. 1. Also, the distances between the alligator jaws 12 and 14 may be variable as represented by the break as shown in the right-hand portion of FIG. 1.

As an alternate arrangement, an indentation may be provided in the backside 54a of the upper jaw 54 in order to facilitate retaining the loop of the suture during knot tying.

Although the present invention has been fully described by way of example with reference to the accompanying drawings, it is to be understood that various changes and modifications will be apparent to those skilled in the art. Therefore, unless otherwise such changes and modifications depart from the scope of the invention, they should be construed as being included therein.

What I claim is:

1. A laparoscopic instrument for use in laparoscopic surgery for forming a suture with a thread, comprising an elongated member having a proximal end and a distal end, a pair of jaw means on said elongated member, each of said pair of jaw means being movable between open and closed positions, one of said pair of jaw means being an end jaw means which is disposed at said distal end and which is operable to engage one part of said thread, the other of said pair of jaw means being an intermediate jaw means which is disposed intermediate said proximal and distal ends and which is operable to engage another part of said thread simultaneously while said one part of said thread is engaged by said one pair of jaw means, and finger grip means on said proximal end of said elongated member, said finger grip means being operably connected to said pair of jaw means for actuating said pair of jaw means between said open and closed positions, whereby said simultaneous engagement of said one and said other part of said thread by said one and said other pair of jaw means respectively facilitates forming of said suture.

2. A laparoscopic instrument according to claim 1, wherein said intermediate jaw means is longitudinally spaced from said end jaw means.

3. A laparoscopic instrument according to claim 1, wherein said finger grip means comprises two finger grip elements selectively operable to independently actuate said intermediate and said end jaw means between their open and closed positions.

4. A laparoscopic instrument according to claim 1, wherein said elongated member has a recess, said intermediate jaw means being disposed in said recess when said intermediate jaw means is in its closed position.

5. A laparoscopic instrument according to claim 1, wherein said intermediate jaw means comprises two jaw elements, one of said jaw elements being mounted for pivotal movement relative to said elongated member, the other of said jaw elements being fixed to said elongated member.

6. A laparoscopic instrument according to claim 5, wherein said elongated member has an outer surface and a recess in said outer surface, said one jaw element being disposed within said recess when said one jaw element is in its closed position.

7. A laparoscopic instrument according to claim 1, wherein said intermediate jaw means comprises two jaw elements each having a mating surface which mate when in said closed position, one of said jaw elements being a pivotal jaw element pivotably mounted relative to said elongated member, said pivotal jaw element having a backside generally parallel to the mating surface of said pivotal jaw element, said backside being generally parallel to said outer surface of said elongated member when said pivotal jaw element is in its closed position.

8. A laparoscopic instrument according to claim 7, wherein said elongated member has an outer surface and a recess in said outer surface, said one jaw element being disposed in said recess such that said backside is generally contiguous with said outer surface of said elongated member when said pivotal jaw element in its closed position.

9. A laparoscopic instrument according to claim 7, wherein said pivotal jaw element protrudes from said recess when said pivotal jaw element is in its open position.

10. A laparoscopic instrument according to claim 1, wherein said intermediate jaw means comprises two jaw elements, one of said jaw elements being a pivotal jaw element pivotably mounted between said open and closed positions, said elongated member having a longitudinal axis, said pivotal jaw element having a jaw axis which is parallel to said longitudinal axis when said pivotal jaw element is in its closed position, said pivotal jaw element having its jaw axis disposed non-parallel to said longitudinal axis when said pivotal jaw element is in its open position.

11. A laparoscopic instrument according to claim 10, wherein said jaw axis of said pivotal jaw element extends at an acute angle relative to said longitudinal axis when said pivotal jaw element is in its open position.

12. A laparoscopic instrument according to claim 10, wherein said jaw axis of said one pivotal jaw element extends at a right angle relative to said longitudinal axis when said pivotal jaw element is in its open position.

13. A laparoscopic instrument according to claim 1, wherein said finger grip means comprises one fixed finger grip fixed to said elongated member and two movable finger grips movable relative to said elongated member.

14. A laparoscopic instrument according to claim 1, wherein said finger grip means comprises two movable finger grip elements such that movement of one finger grip element relative to said elongated member effects opening and closing of one of said pair of jaw means and movement of the other finger grip element relative to said elongated member effects opening and closing of the other of said pair of jaw means.

15. A laparoscopic instrument according to claim 14, wherein said finger grip means further comprises first pivot means pivotably mounting said one movable finger grip element on said elongated member and second pivot means pivotably mounting said other movable finger grip element on said elongated member.

16. A laparoscopic instrument according to claim 15, further comprising biasing means biasing one of said movable finger grip elements in one pivotal direction and biasing means biasing the other of said movable finger grip elements in one pivotal direction.

17. A laparoscopic instrument according to claim 14, wherein said finger grip means further comprises a fixed finger grip element fixed to said elongated member such that a user can selectively grip said fixed finger grip element and said one movable finger grip element to effect actuation of one of said pair of jaw means between its open and closed positions and said user can grip said fixed finger grip element and said other movable finger grip element to effect actuation of the other of said pair of jaw means between its open and closed position.

18. A laparoscopic instrument according to claim 1, further comprising a first rod means longitudinally slidable in said elongated member, said first rod means having one end pivotably connected to said intermediate jaw means, the other end of said first rod means being connected to said finger grip means, a second rod means longitudinally slidable in said elongated member, said second rod means having one end pivotably connected to said end jaw means, the other end of said second rod means being connected to said finger grip means.

19. A laparoscopic instrument according to claim 1, wherein said finger grip means comprises one finger grip operable to move one of said pair of jaw means between its open and closed position and another finger grip is operable to move the other of said pair of jaw means between its open and closed positions, said one and said other finger grips being selectively operable to independently move either said one or said other pair of jaw means between their respective open and closed positions.

* * * * *